United States Patent [19]

Michaels

[11] Patent Number: 4,502,147
[45] Date of Patent: Feb. 26, 1985

[54] MEANS FOR VISUALLY INDICATING AN X-RAY FIELD

[75] Inventor: Terry J. Michaels, Milwaukee, Wis.

[73] Assignee: Charles Lescrenier, Milwaukee, Wis.

[21] Appl. No.: 572,169

[22] Filed: Jan. 18, 1984

Related U.S. Application Data

[63] Continuation-in-part of Ser. No. 406,217, Aug. 9, 1982, abandoned.

[51] Int. Cl.³ .......................... A61B 6/08; G21F 5/04
[52] U.S. Cl. .................................... 378/206; 378/91; 378/150
[58] Field of Search .............. 378/206, 150, 152, 91; 362/32, 259

[56] References Cited

U.S. PATENT DOCUMENTS

| | | | |
|---|---|---|---|
| 2,905,827 | 9/1959 | Graves | 378/150 |
| 3,624,574 | 11/1971 | Montagu . | |
| 3,706,919 | 12/1972 | Abbe . | |
| 3,775,678 | 11/1973 | Abbe . | |
| 3,805,150 | 4/1974 | Abbe . | |
| 3,947,689 | 3/1976 | Wagner | 378/206 |
| 4,135,119 | 1/1979 | Brosens . | |
| 4,142,144 | 2/1979 | Rohr . | |
| 4,167,675 | 9/1979 | Stöberg et al. | 378/206 |
| 4,337,502 | 6/1982 | Lescrenier | 362/32 |

OTHER PUBLICATIONS

"Preliminary Date Sheet", General Scanning, Inc.
"Closing The Loop On Galvo Scanners", Grenda & Brosens, General Scanning, Inc.
"Applications of Galvanometers to Laser Scanning", Brosens & Grenda, General Scanning, Inc., Aug. 19–23, 1974.
"Series G Optical Scanners", General Scanning, Inc., 8/79.

Primary Examiner—Alfred E. Smith
Assistant Examiner—T. N. Grigsby
Attorney, Agent, or Firm—Andrus, Sceales, Starke & Sawall

[57] ABSTRACT

A visual indicator for an X-ray field includes a light generator providing a beam of light. The light is provided to a first mirror that moves about an axis normal to the beam of light to deflect the beam. The deflected beam is applied to a second mirror that moves about an axis normal to the first axis and applies the beam of light to a mirror on the axis of the X-ray beam for reflection onto the X-ray field. The mirrors are controlled by signals indicative of the field defining collimator leaves to cause the light beam to trace out the field defining by the collimator leaves.

20 Claims, 11 Drawing Figures

MEANS FOR VISUALLY INDICATING AN X-RAY FIELD

The present application is a continuation-in-part application of U.S. patent application Ser. No. 406,217, filed Aug. 9, 1982 and now abandoned.

X-ray generators, particularly those used for medical purposes, employ a collimator that establishes the area or field exposed to the X-rays. Such a collimator typically includes a plurality of movable leaves that are opened and closed manually or automatically to establish the exposure area in accordance with the type of X-ray being taken, the size of film in the film cassette or magazine, the distance of the X-ray generator to the film, and other factors.

As the X-ray beam is not visible to the eye, it is necessary to provide some means of visually indicating the exposure field established by the collimator. In present X-ray collimators, the field is usually illuminated with visible light. An incandescent lamp is so arranged in the collimator that the light illuminates the same area exposed to the X-rays. For this purpose, a mirror is mounted along the axis of the X-ray beam at a 45° angle to receive light from an adjacent lamp and shine it along the axis of the X-ray beam onto the area to be exposed. The size of the beam of light will be defined by the collimator leaves in the same manner as the X-ray beam so that the lighted area indicates the size of the X-ray field.

Such a system is simple since the same beam defining system is used for both the X-ray field and the lighted area. However, it has been difficult to obtain an adequate intensity of illumination of the lighted area. It has been particularly difficult to obtain adequate sharpness and definition at the edges of the field. And, it is the edges that actually define the limits of the field.

In an effort to provide sufficient intensity and sharpness, quartz-halogen lamps having very small filament size and high thermal dissipation must be used. The lamps are expensive and are best used only intermittently to limit heat buildup and extend service life. Even with such lamps, it is often difficult to see the edges of the X-ray beam, particularly at the ambient light levels often encountered during manual X-ray procedures.

It is, therefore, the object of the present invention to provide an improved apparatus for visually indicating an X-ray field that overcomes the foregoing shortcomings. The present invention provides a clear, accurate definition of the X-ray field, even in conditions of high ambient light. A particularly advantageous feature of the present invention is that it can sharply define the edges of the X-ray field without the need to illuminate the remaining, central portions of the field. The means of the present invention may be used as frequently or continuously as desired, without undesirable thermal or other effects or a lessening of service life.

Briefly, the present invention contemplates apparatus for visually indicating the field produced by an X-ray beam passing through an adjustable, field defining collimator of the X-ray equipment. The collimator contains a means for producing signals indicative of the dimensions of the field and the X-ray equipment has a mirror along the axis of the X-ray beam for reflecting a light beam onto the field.

The apparatus includes a light source generating a beam of light along the path. A first mirror receives the beam to reflect same at an angle to the path. A first drive means moves the first mirror about an axis normal to the path of generation of the light beam responsive to a first signal to arcuately move the light beam. A second mirror receives the beam of light off the first mirror and further reflects same. A second drive means moves the second mirror about an axis parallel to the path of generation of the light beam responsive to a second signal to arcuately move the reflected light beam and to apply the reflected light beam to the mirror in the X-ray apparatus for reflection onto the field. A signal generator generates first and second signals to said first and second drive means responsive to the field dimension signals that cause said drive means to move the mirrors so that the light beam traces out the dimensions of the field defined by the collimator. The signal generating means may be of either the analog or digital type.

The invention will be further explained by the aid of the accompanying drawing in which.

Figure 1:
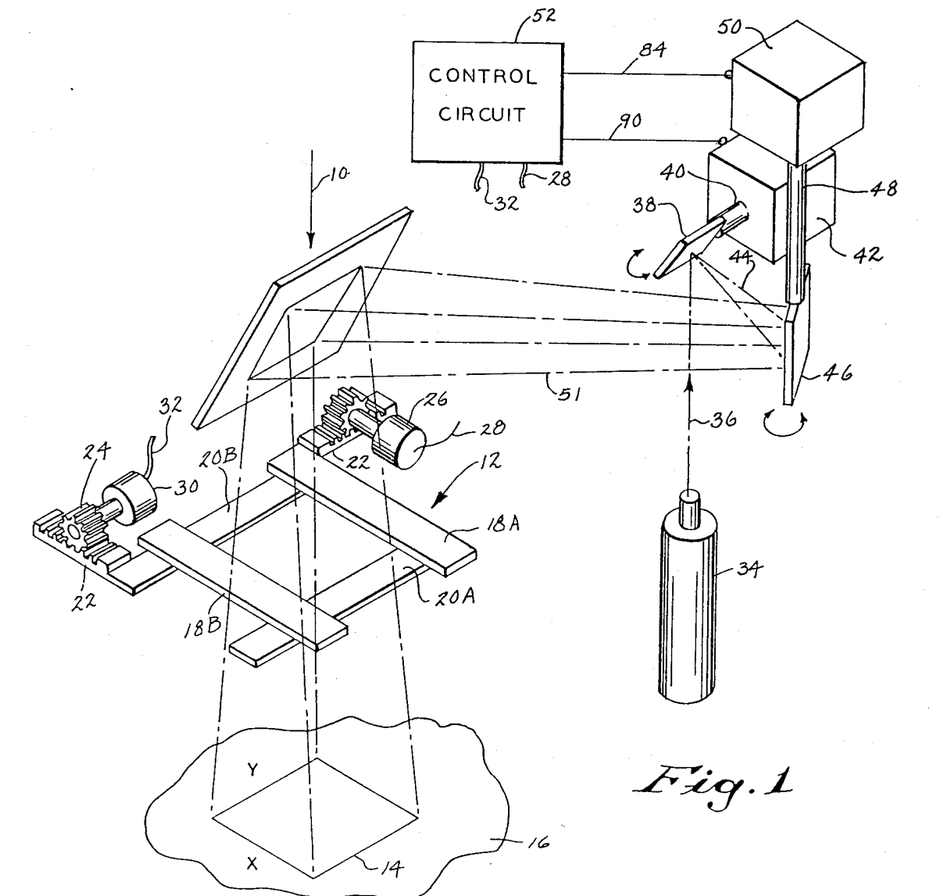
FIG. 1 is a somewaht schematic, perspective view showing portions of the apparatus of the present invention.

In FIG. 1, an X-ray generator, not shown, provides an X-ray beam along axis 10 through collimator 12 to X-ray field 14 on the body of a patient 16. Collimator 12 contains two pairs of leaves 18A and 18B and 20A and 20B. The leaves of each pair are coordinately moved toward and away from each other by conventional means, not shown, so that each pair establishes one dimension of the X-ray field 14. For purposes of explanation, leaves 18 may be deemed to establish the Y dimension of field 14 and leaves 20, the X dimension.

For purposes hereinafter indicated, an electric signal is provided corresponding to the position of each pair of leaves, as by potentiometers driven by racks 22 and pinions 24. Potentiometer 26 provides a signal in conductor 28 indicative of the position of leaves 18 and the Y dimension of field 14 and potentiometer 30 provides a signal in conductor 32 indicative of the position of leaves 20 and the X dimension of field 14. In the case of an automatic collimation system, the signals in conductors 28 and 32 may be the position feedback signals from the collimator leaves employed in the automatic system.

The visual indicating apparatus of the present invention includes a light source 34 that may typically comprises a laser of the helium-neon type. Light source 34 provides a narrow beam 36 of coherent light. In the illustrated exemplary embodiment, the beam 36 of light source 34 shines vertically upward.

The beam 36 of light source 34 is applied to a first mirror 38 to oscillate about a horizontal axis in either direction from a central position lying at 45° to light beam 36. Mirror 38 may be mounted on shaft 40 turned by electrodynamic drive 42. Drive 42 may comprise a galvanometric movement having a magnet and associated coil that is energized to rotate mirror 38. The rotary actuators sold by General Scanning, Inc. of Watertown, Mass. as the Series EM are suitable for use as drive 42. Other suitable drives are those used to drive pen motors in electrocardiographs and electroencephalographs. Drive 42 is energized in a manner hereinafter described to rotate shaft 40 and oscillate mirror 38. When in the central position mirror 38 will provide a horizontal beam of reflected light.

The light 44 reflected off mirror 38 is applied to a second mirror 46 that oscillates about a vertical axis in either direction from a central position lying at 45° to the horizontal light beam 44. Mirror 46 may be mounted on shaft 48 turned by electrodynamic drive 50 that may be similar to drive 42.

The light beam 51 reflected off mirror 46 is applied to mirror 54 that is located along the axis 10 and lies at a 45° angle with respect thereto. Mirror 54 is transparent to the X-ray beam.

Figure 2:
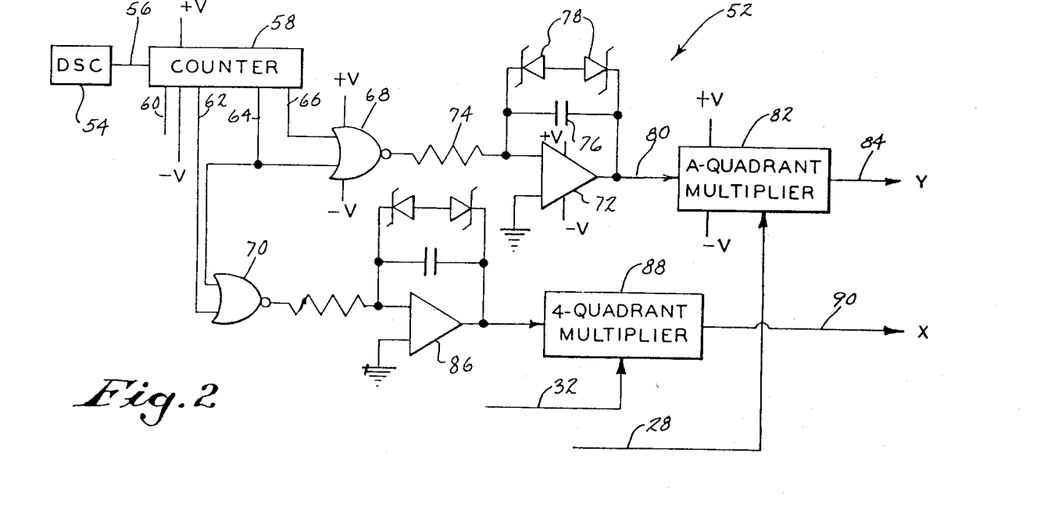
FIG. 2 is a schematic circuit diagram showing circuitry incorporated in the apparatus of the present invention.

FIG. 2 shows circuitry 52 for energizing electrodynamic drives 42 and 50. An oscillator, or free running clock, 55 produces a square wave pulse train signal in conductor 56 to counter 58. Counter 58 may be a divide-by-four counter providing a decoded output at a plurality of output terminals, 60, 62, 64, and 66. With a decoded output, the output terminals each sequentially provide a divide-by-four output. Thus at a first pulse in the signal in conductor 56, output 60 provides an output pulse; for a second pulse in conductor 56, output 62 provides an output pulse; and the third and fourth pulses in conductor 56 provide output pulses in outputs 64 and 66, respectively. At the fifth pulse in conductor 56, output 60 again provides an output pulse. At the sixth pulse in conductor 56, output 62 again provides an output pulse, and so on. Counter 58 may comprise the circuit element sold by RCA under the designation CD4022 or that sold by Motorola Corporation under the designation MC14022.

Output 64 of counter 58 is conncted to one input of NOR gates 68 and 70. Output 62 is connected to the other input of NOR gate 70 and output 66 is connected to the other input of NOR gate 68.

The outputs of counter 58 and NOR gates 68 and 70 are referenced to the negative voltage supply so that the outputs of each NOR gate is a bipolarity pulse train of 50% duty cycle.

NOR gate 68 is connected to operational amplifier 72 through resistor 74. Capacitor 76 is connected in the feedback of operational amplifier 72 so that the element functions as an integrator for the square wave pulses in conductor 56. The integration rate, or slope of the output signal of amplifier 72 is determined by the relative magnitudes of resistor 74 and capacitor 76. Breakover Zener diodes 78 in parallel with capacitor 78 limit the output of operational amplifier 72.

The output of operational amplifier 72 is provided in conductor 80 to one input of a four quadrant multiplier 82. The other input to four quadrant multiplier 82 is the signal from potentiometer 26 in conductor 28. The designation "four quadrant" indicates that the element performs algebraic multiplication, accounting for not only the magnitudes but also the algebraic signas of the signals in conductors 80 and 28. Multiplier 82 may comprise the element sold by RCA under the designation CA3080 or that sold by Motorola under the designation MC1495. The output of four quadrant multiplier is provided in conductor 84 to coil 44 of electrodynamic drive 50. While termed a "multiplier" above, it will be appreciated that the magnitude of the signal in conductor 80 is fixed by Zener diodes 78 so that the element 82 actually functions in the nature of a variable gain amplifier for the signal in conductor 28. In a similar manner, the output of NOR gate 70 is connected through an integrating operational amplifier 86 to one input to four quadrant multiplier 88. The other input to four quadrant multiplier 88 comprises the signal in conductor 32 from potentiometer 30. The output of multiplier 88 is provided in conductor 90 to electrodynamic drive 42.

Figures 3, 4, 5, 6:
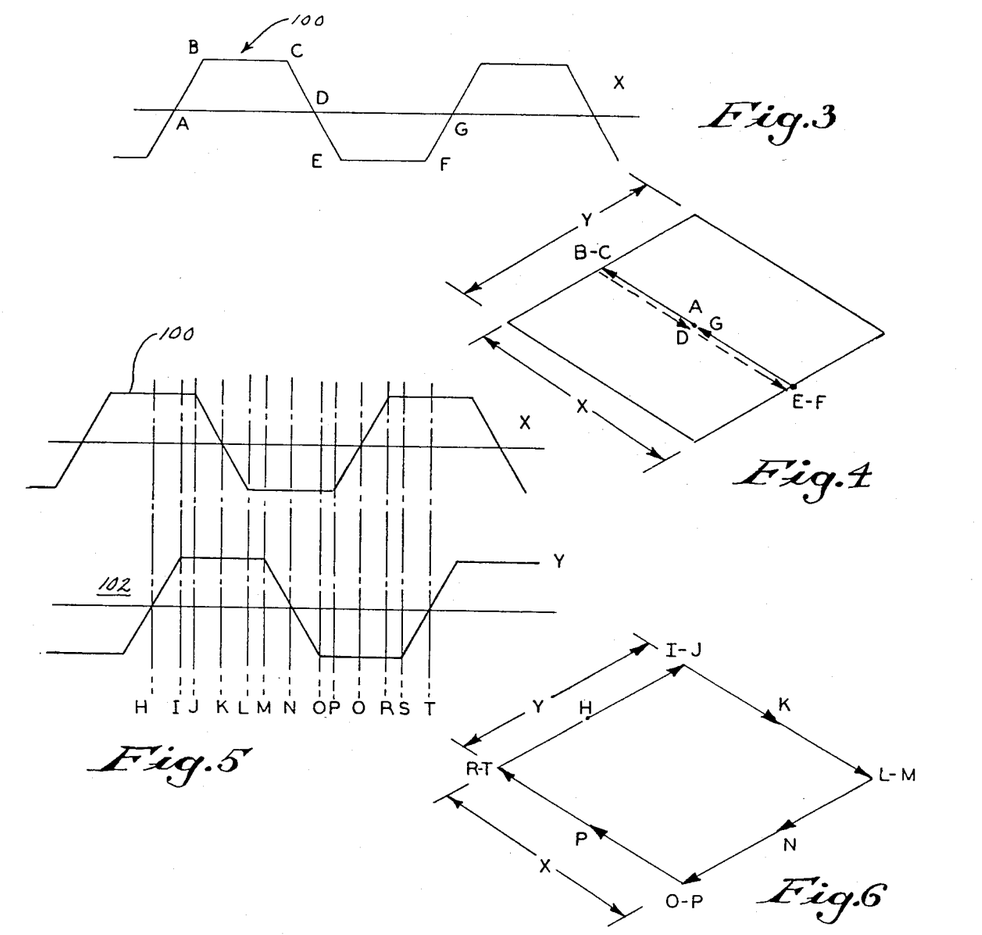
FIG. 3 is a graph of an output signal from the circuitry shown in FIG. 2.
FIG. 4 is a schematic diagram showing the operation of the visual indicating apparatus of the present invention in accordance with the signal shown in FIG. 3.
FIG. 5 is a graph, similar to FIG. 3, showing a pair of output signals of the circuitry of FIG. 2.
FIG. 6 is a schematic diagram illustrating the operation of the visual indicating apparatus of the present invention in accordance with the signal shown in FIG. 5.

The output signals in conductors 84 and 90 are shown in FIG. 5 as signals 100 and 102, respectively. Signals 100 and 102 are phase displaced 90° through the operation of counter 58 and NOR gates 68 and 70. The magnitude of signals 100 and 102 are determined by the signals in conductors 28 and 32, respectively, indicative of the X and Y dimensions of field 14. The slope of the intermediate portions of the signal is determined by the integrators comprised of amplifiers 72, 86 and the associated R-C circuits.

The circuit described above has little d.c. drift and thus will possess a high degree of stability.

The operation of the visual indicating apparatus shown in FIGS. 1 and 2 is as follows. If neither electrodynamic drive 42 of electrodynamic drive 50 is energized, mirrors 38 and 46 are in their central position. The light beam 36 is reflected off mirrors 38 and 46, as light beams 44 and 52 and is reflected off mirror 54 along the axis 10 of the X-ray beam to appear as a dot in the center of field 14.

Assume a condition in which electrodynamic drive 42 is energized by signal 100 in conductor 90 and there is no signal in conductor 84. At point A in signal 100, as shown in FIG. 3, the level of signal 100 is zero and mirror 38 will be in the central position in which it is at a 45° angle to light beam 36. As mirror 46 is in the central position, the light beam reflected from mirror 54 will be centered in field 14 to produce a dot of light shown in FIG. 4 as A. As signal 100 increases in magnitude in one polarity from A to B, electrodynamic drive 42 will become increasingly energized and will rotate mirror 38 in one direction from the central position. A corresponding deflection of the reflected light beam 44 from mirror 38 out of the horizontal plane will result. With mirrors 46 and 54 stationary, the movement of mirror 38 will cause the light beam reflected off mirror 54 to trace out line A-B toward the edge of field 14, as shown in FIG. 4. The amount of movement of mirror 38 and the length of the trace A-B is determined by the magnitude of signal 100 at point B, which, in turn, is determined by the magnitude of the signal in conductor 32 that indicates the position of collimator leaves 20 that determine the corresponding dimension of field 14. By appropriate scaling of one or more of the signal, as by a potentiometer or other means, or by adjustment of the operating parameters of circuit 52 or drive 42, point B may be caused to lie on the periphery of field 14.

From point B to point C, signal 100 and the energization of drive 42 is constant. This will retain mirror 30 in the deflected position and the light beam reflected off mirror 54 will be retained at point B-C to produce a stationary dot of light on one side of the periphery of field 14.

As the energization of drive 42 is returned to zero by the portion C-D of signal 100, mirror 38 moves from the deflected position back to the central position. This returns the reflected light beam 44 to the horizontal position and causes the light beam to trace out a line C-D back to the center of field 14. It will be appreciated that while lines A-B and C-D are shown slightly displaced in FIG. 4, they are actually congruent in field 14 in the operation of the visual indicating apparatus.

When signal 100 changes to the opposite polarity during the half cycle D, E, F, G, mirror 38 is rotated by electrodynamic drive in the opposite direction so that the light beam reflected off mirror 54 traces out a line in the opposite direction from the central position A-D in field 14, as shown by D-E-F-G in FIG. 4. The point E-F lies on the periphery of field 14 on the opposite side from point B-C. It will be appreciated from FIG. 4 that the light trace from B-C to E-F is an indication of the X dimension of field 14.

FIGS. 5 and 6 show the use of output signals 100 and 102 to both electrodynamic drive 42 and electrodynamic drive 50 and the resulting operation of visual indication apparatus of the present invention in defining field 14. With signal 102 applied to electrodynamic drive 50, both mirror 38 and mirror 46 will be deflected. In a manner similar to that described above in connection with signal 100, the magnitude of signal 102 is determined by the magnitude of the signal in conductor 28. The magnitude of the signal in conductor 28 corresponds to the position of collimator leaves 18 that determines the Y dimension of field 14.

Assume a starting position H. At this point, signal 100 is at the maximum value deflecting mirror 38 to one extreme position. The value of signal 102 is zero so that mirror 46 is not deflected. By analogy to FIGS. 3 and 4, it will be appreciated that the light beam reflected off mirror 54 will form a dot at point H in FIG. 6, that corresponding generally to point B-C in FIG. 4. Point H is on the periphery of field 14 at one end of the X dimension.

As signal 102 increases in the segment H-I, electrodynamic drive 50 will be energized to rotate mirror 46 out of the central position about the vertical axis. This deflection of mirror 46 moves the light beam along a trace from point H to Point I. Point I is at one end of Y dimension of field 14. The trace H-I forms a segment of the periphery of field 14 and point I marks a corner of field 14.

During the time interval I-J, both signals 100 and 102 are at maximum positive value. Mirrors 36 and 46 are held in their deflected position. There is no movement of the light beam reflected off mirror 54 and it remains at point I. This retention, or "dwell" of the light beam at point I assists in clearly demarcating the corners of field 14.

In the segment J-K of signal 100, that signal is decreasing in positive magnitude, to the zero signal condition at point K. The signal segment J-K causes electrodynamic drive 42 mirror 38 to return to the central, undeflected position. Mirror 46 remains in the deflected condition since the magnitude of signal 102 has not changed. The light beam reflected off mirror 54 traces out the segment J-K in FIG. 6 forming a segment of the periphery of field 14.

The polarity of signal 100 changes at point K. The opposite polarity signal 100 applied to electrodynamic drive 42 deflects mirror 38 in the opposite direction so that light beam 34 traces out the line K-L along the periphery of field 14 to complete the indication of the X dimension of field 14.

During the segment L-M, signal 100 is a constant magnitude negative signal. Signal 102 is a constant magnitude positive signal. There is no movement of mirrors 38 and 46 from their deflected positions due to the constant magnitude signals to electrodynamic drives 42 and 50 so that the light beam reflected off mirror 54 dwells at point L-M for this period to demarcate a second corner of field 14.

During the segment M-N, signal 102 is decreasing in magnitude to the zero condition at point N. This reduction in the energization of electrodynamic drive 50 causes mirror 46 to return to the central position. The light beam reflected off mirror 54 traces out the segment M-N.

The operation of electrodynamic drives 42 and 50 and mirrors 38 and 46 responsive to the energization by signals 100 and 102 occurring in the segments N-T are analogous to those described in detail above. The trace of the light beam reflected off mirror 54 in all of the segments shown in FIG. 6 completely defines the periphery of field 14 and thus visually indicates the X-ray field established by collimator leaves 18 and 20.

The trace of the light beam repeats itself with the signals commencing at point H in FIG. 6 to repeat the visual indication of field 14. Signals 100 and 102 may typically have a frequency of between 15 and 30 Hz, for example 20 Hz, so that the rapidity of movement of the light beam in making the trace H and T exceeds that which the human eye can follow. The X-ray technician thus sees a square or rectangle of visible light clearly indicating the periphery of field 14. Light beam 36 may be made sufficiently intense that the trace can be easily seen in all ambient light levels likely to be encountered.

The dimensions of the pattern traced by the light reflected off mirror 54 are determined by the signals in conductors 28 and 32 from potentiometers 26 and 30 to multipliers 82 and 88. As the spacing between the collimator leaves 18 and 20 is varied, the amplitude of the signals to electrodynamic drives 42 and 50 from multipliers 82 and 88 are proportionately varied so that the pattern traced by the light beam reflected off mirror 54 always defines the periphery of the X-ray field 14.

The slope of the portions of signals 100 and 102 such as C-D-E is selected in accordance with the inertial properties of electrodynamic drives 42 and 50 as, for example, to provide constant velocity to the movement of mirrors 38 and 46, thereby to lessen or avoid undampened oscillations or other undesired conditions in electrodynamic drives 42 and 50.

Figure 7:
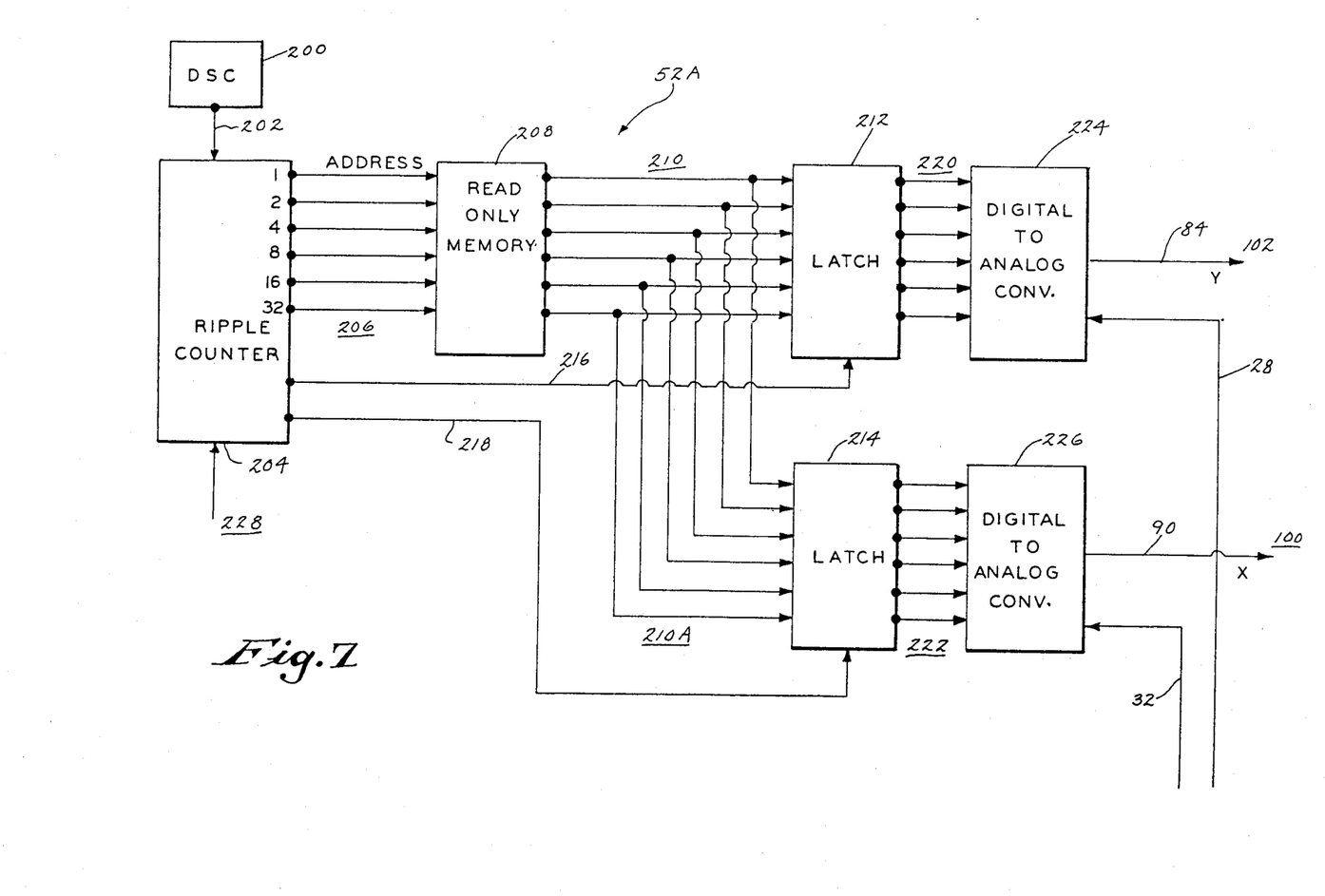
FIG. 7 is a schematic circuit diagram showing an alternative embodiment of the circuitry for the apparatus of the present invention.

FIG. 7 shows an alternative embodiment of the circuitry 52A for energizing electrodynamic drives 42 and 50 in which the signal values needed to position mirrors 38 and 46 for the X and Y dimensions of field 14 are digitally encoded and stored in a read only memory. These values generate signals for drives 42 and 50 as by their periodic supply to a pair of digital/analog converters to generate signals 100A and 102A shown in FIG. 8 and corresponding to signals 100 and 102 shown in FIG. 5.

In the circuitry shown in FIG. 7, the pulse train output of oscillator 200 in conductor 202 is connected to ripple or binary counter 204 that counts the pulses in conductor 202. Counter 204 may be that element sold by Motorola Corporation under the designation MC14024B. The output of ripple counter 204, indicative of the counting occurring in the counter, is provided in parallel conductors 206 to the address input of read only memory for the digitally encoded values for the X and Y dimensions of field 14. The digital values so accessed are provided at the output of read only memory 208 in parallel conductors 210. If read only memory 208 has a sufficiently large number of input and outputs, a digital value for both the X and Y dimensions, i.e. for signals 100A and 102A, may be simultaneously provided at the output of read only memory 208. For a small number of input and outputs, read only memory may be so addressed as to alternately provide the digitally encoded values for signal 100A (X dimension) and for signal 102A (Y dimension). For example, for even numbered counts in conductors 206, the digital value for signal 100A may be provided in conductors 210. For odd numbered counts in conductor 206, the digital values for signal 102A are provided in conductors 210. FIG. 7 shows circuitry incorporating this latter approach.

The output of read only memory 208 is provided in parallel to two latch circuits 210 and 214 in conductors 210 and 210A. Latch circuits 210 and 214 are alternately operated by the signal from counter 204 to latch 212 in conductor 216 and the signal from counter 204 in conductor 218 to latch 214. The signals in conductors 216 and 218 indicate whether the count in counter 204 is odd or even and operates one of the latches for all the odd numbers and the other of the latches for all the even numbers. Through the alternate odd-even operation of the latches, latch 212 accepts all digitally encoded values from read only memory 208 for signal 102A and latch 214 accepts all the digitally encoded values from read only memory 208 for signal 100A.

The digital output of latch 212 is provided in conductors 220 to multiplying digital/analog converter 224 that also receives the signal in conductor 28 from potentiometer 26 indicating the position of leaves 18. Digital/analog converter 224 generates signal 102A in conductor 84 to electrodynamic drive 50. As the analog signal produced responsive to the signal in conductors 220 has fixed magnitude properties, the output of digital analog converter 224 is directly proportional, in magnitude, to the signal in conductor 28 from collimator potentiometer 26. The digital output of latch 214 is provided in conductors 222 to multiplying digital/analog converter 226. Digital/analog converter 226 also receives the signal in conductor 32 from potentiometer 30 associated with collimator leaves 20. Digital/analog converter 226 generates signal 100A in conductor 90 to electrodynamic drive 42.

Figure 8:
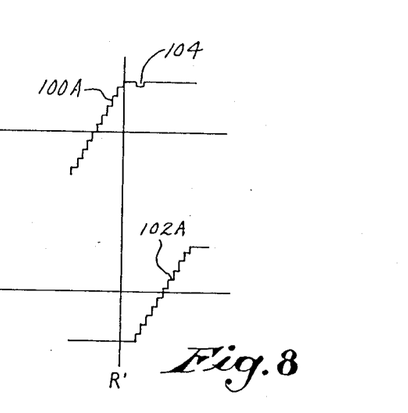
FIG. 8 is a graph showing portions of the signals generated by the apparatus shown in FIG. 7.

FIG. 8 is a fragmentary graph showing the signals 100A and 102A provided in conductors 90 and 84, respectively, by the circuitry of FIG. 7. The signals correspond to those of FIG. 5 except that they are incrementally formed by the digitally encoded values of read only memory 208. As with signals 100 and 102 shown in FIG. 5 the magnitudes of the signals in conductors 28 and 32 so that the trace of the light beam reflected off mirror 54 visually indicates field 14. The size of the incremental steps in signals 100A and 102A is selected such that the inertia of the moving parts of electrodynamic drives 42 and 50 provides an electromechanical filtering action that smooths the incremental steps when mirrors 38 and 46 are operated.

The use of read only memory 208 provides additional flexibility in the formation of signals 100 and 102 over that which can be conveniently obtained with the analog circuitry of FIG. 2. For example, the values stored in read only memory 208 may be adjusted to compensate for non-linearity in the operation of electrodynamic drives 42 and 50 due to hysteresis in the galvanometric movements. The same is true of undampened oscillations in drives 42 and 50 termed "ringing". These typically occur in a transition from a rising or falling signal to a constant magnitude signal as at point R' in FIG. 8. The oscillation may be damped by providing the slight reduction 104 after point R' has been attained, as shown in FIG. 8.

Read only memory 208 may also contain digitally encoded values that provide signals to electrodynamic drives 42 and 50 to cause mirrors 38 and 46 to make light beam traces in field 14 other than about the periphery of the field. For example, read only memory 208 may operate drives 42 and 50 so that the mirrors 38 and 46 generate a cross or other center marker for field 14. A signal in conductor 228 to counter 204 alters the output of counter 204 to provide a band of numbers accessing the portion of read only memory 208 containing the digitally encoded signals necessary for such a light beam trace. In a similar manner read only memory 208 can contain digitally encoded values that generate light traces in the form of numbers, letters, or words, such as "no film" on field 14. And, circuitry 52A can switch between or among various forms of light beam traces.

To maintain the proper correlation between the position of collimator leaves 18 and 20 defining X-ray field 14 and the trace of the light beam reflected off mirror 54 visually indicating that field, it is necessary that the point of origin of the light beam be at an optical distance from mirror 54 equal to or less than the distance from the mirror to the X-ray source. If the point of origin of the light beam is further away than the point of origin of X-ray source, collimator 12 will block the light and it will not properly indicate field 14. For the X dimension, the point of origin is mirror 38. For the Y dimension, the point of origin is mirror 46. In a practical embodiment of the visual indicating apparatus, mirrors 38 and 46 may be quite close together so that the points of origin tend to be the same.

The necessary positioning of the visual indicating apparatus may create a physically awkward structure. It may be more convenient to place mirrors 38 and 46 and the associated electrodynamic drives 42 and 50, outside the X-ray equipment to facilitate the design, use, and maintenance of the apparatus. However, this may cause the optical distance of the points of origin to be too great.

Figure 9:
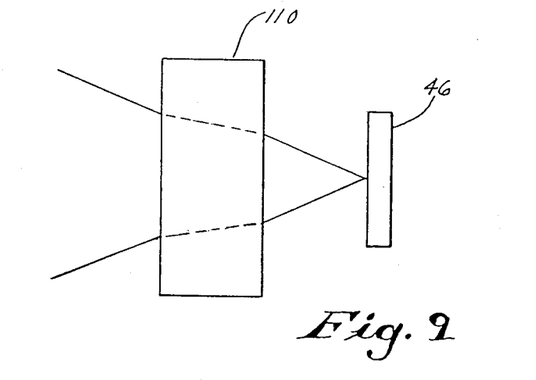
FIG. 9 is a perspective, somewhat diagrammatic view showing modification of the apparatus to maintain correct optical distances.

In such a case, an optical spacer 110 made of the transparent material having a high index of refraction may be employed, as shown in FIG. 9. Such a material may be similar to that used in eyeglasses in which the index of refraction may approach 2.5. The use of such a material provides an effective shortening of the optical path while allowing the physical path to be sufficiently long to permit external mounting of the light source.

Or, the appropriate compensation may be applied to the signals in conductors 84 and 90 used to drive electrodynamic drives 42 and 50.

Figure 10:
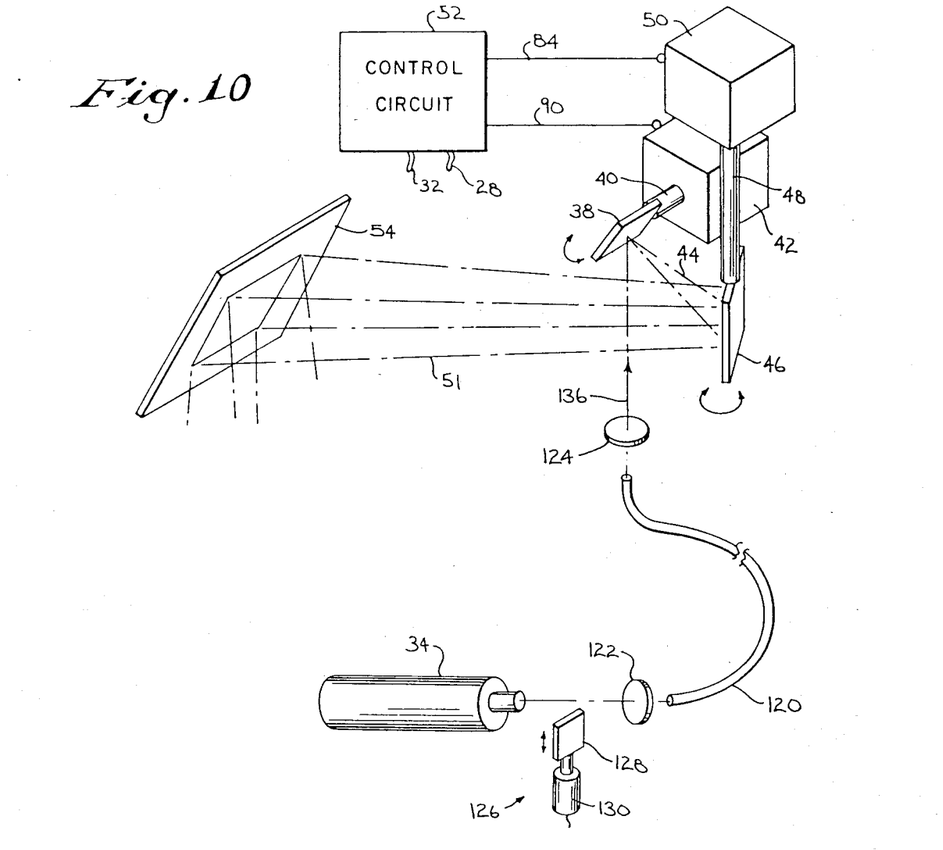
FIG. 10 is a schematic view of a modification of the apparatus of the invention.

In another modification of the invention, shown in FIG. 10, light source 34 may be placed at some convenient location away from the collimator and coupled to the remaining portions of the visual indicating apparatus by optical fiber cable 120 through lenses 122 and 124. The output end of cable 120 occupies the position of light source 34.

For safety purposes, the intensity of the light from a light source 34, such as a laser, to patient 16 is limited by regulation. When the dimensions of field 14 are small or the movement of light beam 36 by mirrors 38 and 46 is slow, the intensity of the light may exceed permissible values.

Figure 11:
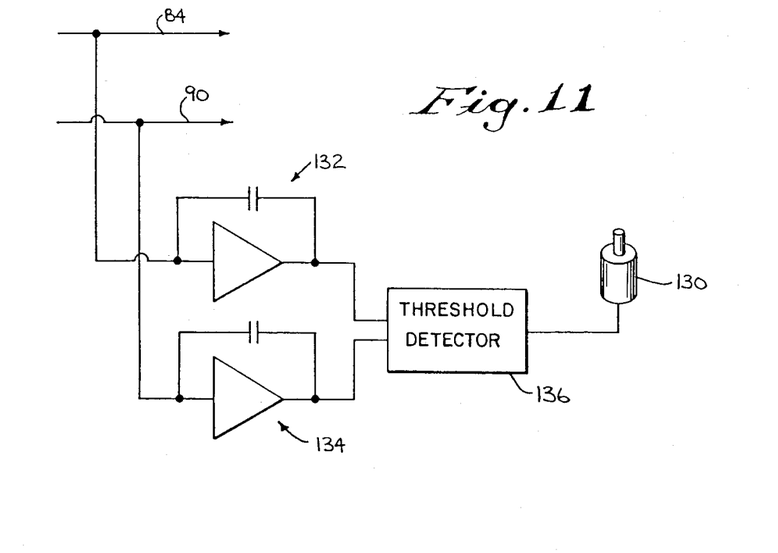
FIG. 11 is a schematic circuit diagram showing a modification of the circuitry of FIG. 2 for use with the apparatus of FIG. 10.

To reduce the intensity of the light applied to patient 16, an optical attenuator 126 may be placed along the light path, as at the output of light source 34 shown in FIG. 10. Attenuator 126 may include a neutral density filter 128 coupled to actuator 130 that inserts and removes it from the light path. To control actuator 130, the output signals from circuitry 52 or 52A in conductors 84 and 90 are applied to integrators 132 and 134, as shown in FIG. 11. The outputs of integrators 132 and 134 are connected to threshold detector 136, the output of which is connected to actuator 130. The circuitry shown in FIG. 11 can operate in a failsafe mode such that unless the dimensions of field 14 and the movement rate of mirrors 38 and 46 are above a certain level, as established by threshold detector 136, filter 128 is inserted in the light path.

Various modes of carrying out the invention are contemplated as being within the scope of the following claims particularly pointing out and distinctly claiming the subject matter which is regarded as the invention.

I claim:

1. Apparatus for providing a visual indication in the field produced by an X-ray beam having a mirror on the axis thereof for reflecting a light beam onto the field, said apparatus comprising:
   a light source generating a light beam along a path;
   a first means for receiving said beam and for deflecting same at an angle to said path, said first deflection means being responsive to a first signal for arcuately moving the light beam;
   a second means for receiving the beam of light deflected by said first deflection means and for futher deflecting same to apply said light beam to the mirror in the X-ray beam for reflection onto the field, said second deflection means being responsive to a second signal to arcuately move the light beam; and
   signal generating means for generating the first and second signals for energizing said first and second deflection means to move the light beam about the field to provide the visual indication.

2. A visual indication apparatus of claim 1 wherein said first and second deflection means comprise first and second mirrors and first and second signal responsive drive means.

3. The apparatus according to claim 2 wherein said first drive means is further defined as moving said first mirror about an axis normal to the path of generation of the light beam and said second drive means is further defined as moving said second mirror about an axis parallel to the path of generation of light beam.

4. The visual indication apparatus of claim 3 wherein said drive means comprises electrodynamic drive means.

5. The visual indication apparatus of claim 4 wherein said electrodynamic drive means comprise galvanometric means.

6. The visual indication apparatus of claim 1 further defined as providing a visual indication of the field produced by the X-ray beam passing through a field defining collimator of X-ray equipment producing signals corresponding to the dimensions of the field and wherein said signal generating means generates the first and second signals responsive to the field dimension signals of the X-ray equipment for energizing said first and second deflection means to move the light beam about the field in a field defining manner.

7. The visual indication apparatus of claim 6 wherein said signal generating means includes means for generating a pair of signals displaced by 90° and supplying one of said signals to each of said first and second deflection means.

8. The visual indication apparatus of claim 4 wherein said signals are electric signals and wherein said signal generating means is responsive to said field dimension signals for controlling the magnitude of said signals to said first and second deflection means and the amount of deflection in said means.

9. The visual indication apparatus of claim 7 wherein the field is rectilinear and said signal generating means so forms the displaced signals as to provide overlapping regions of constant magnitude signals that retain the reflected light beam in the corners of the field.

10. The visual indication apparatus of claim 7 wherein said signal generating means comprises means providing a train of pulses; means generating a pair of signals displaced by 90° from said pulse train; and means responsive to said field dimension signals for altering the magnitude of said pair of displaced signals in accordance therewith.

11. The visual indication apparatus of claim 7 including means for providing a slope to said pair of signals intermediate constant magnitude portions.

12. The visual indication apparatus of claim 10 wherein said means providing a pair of signals includes a counter coupled to said pulse train providing means, the output of said counter being provided to logic elements providing said pair of signals.

13. The visual indication apparatus of claim 10 wherein said means for altering the magnitude of said signals comprises a multiplier.

14. The visual indication apparatus of claim 11 wherein said means providing said slope comprises an operational amplifier having resistive-capacitive means operatively associated therewith.

15. The visual indication means of claim 7 wherein said signal generating means generating a pair of signals comprises accessing means connected to a memory means generating said signals, said memory means being connected to circuit means providing said pair of signals, said field dimension signals being connected to said circuit means for altering the magnitude of said pair of signals.

16. The visual indication means of claim 15 wherein said circuit means provides said pair of signals in digital form and said circuit means is connected to digital-analog converters providing said pair of signals to said deflection means.

17. The visual indication means of claim 1 including optical spacer means in the path of one of the light beam or deflected beams.

18. The visual indication means of claim 1 wherein said light source includes light conducting means for generating said light beam.

19. The visual indication means of claim 1 including light attenuating means insertable in the path of said light beam.

20. The visual indication means of claim 19 including means for operating said light attenuating means responsive to said first and second signals for inserting said light attenuating means in said light beam to control the intensity of the light beam.

* * * * *